United States Patent [19]

Davis et al.

[11] 4,083,948

[45] Apr. 11, 1978

[54] BENZODIAZEPINE RADIOIMMUNOASSAY USING I125-LABEL

[75] Inventors: Raymond Vincent Davis; Rodney Ian Fryer, both of North Caldwell, N.J.

[73] Assignee: Hoffmann-La Roche, Inc., Nutley, N.J.

[21] Appl. No.: 784,101

[22] Filed: Apr. 4, 1977

[51] Int. Cl.$^2$ .................... A61K 43/00; G01N 33/16; C07G 7/00

[52] U.S. Cl. ..................... 424/1; 23/230 B; 260/112 R; 260/239.3 D; 424/8; 424/12

[58] Field of Search .............. 424/1, 1.5, 12, 18; 260/239.3 D, 112 R; 23/230 B

[56] References Cited

U.S. PATENT DOCUMENTS

| | | | |
|---|---|---|---|
| 3,335,295 | 8/1967 | Sternbach et al. | 260/239.3 D |
| 3,336,296 | 8/1967 | Bell et al. | 260/239.3 D |
| 3,338,886 | 8/1967 | Berger et al. | 260/239.3 D |
| 3,546,212 | 12/1970 | Felix et al. | 260/239.3 D |
| 4,022,878 | 5/1977 | Gross | 424/1.5 |

OTHER PUBLICATIONS

Rejent et al., Clinical Chemistry, vol. 22, No. 6, June, 1976, pp. 889–891.

Dixon et al., Journal of Pharmaceutical Sciences, vol. 64, No. 6, June, 1975, pp. 937–939.

Peskar et al., The Journal of Pharmacology and Experimental Therapeutics, vol. 186, No. 1, July, 1973, pp. 167–172.

*Primary Examiner*—Benjamin R. Padgett
*Assistant Examiner*—Christine M. Nucker
*Attorney, Agent, or Firm*—Samuel L. Welt; George M. Gould

[57] ABSTRACT

An improved radioimmunoassay for benzodiazepines such as diazepam, chlordiazepoxide, oxazepam, demoxepam and metabolites thereof is disclosed. Such immunoassay employs novel $^{125}$I-labelled 4'-hydroxy derivatives of these compounds as tracer.

15 Claims, No Drawings

BENZODIAZEPINE RADIOIMMUNOASSAY USING I125-LABEL

BACKGROUND OF THE INVENTION

The development of immunoassy provides a powerful method for the measurement of drug levels in biological fluids. The extensive clinical use and continued development of benzodiazepines as a class of drugs makes it desirable that immunoassays be developed for these compounds.

Several such immunoassays directed to benzodiazepines have been developed and reported in the literature. Thus Peskar and Spector described a radioimmunoassay procedure useful in detecting nanogram amounts of diazepam or N-desmethyldiazepam in plasma samples in J. Pharmacol. Exp. Ther. 186, 167 (1973). This assay utilized $^{14}C$-diazepam as the tracer. Antibodies were elicited using either 5- [3-(4-aminophenylazo)-4-hydroxyphenyl] -7-chloro-1,3-dihydro-1-methyl-2H-1,4-benzodiazepin-2-one or 7-amino-5-(2-chlorophenyl)-3H-1,4-benzodiazepin-2-(1H)-one as haptens which were subsequently coupled to bovine serum albumin (BSA) to form the desired immunogens.

Subsequently, Dixon et al. reported in J. Pharm. Sci. 64, 937 (1975) of a radioimmunoassay for chlordiazepoxide in plasma. Once again the tracer compound was a $^{14}C$-labelled compound. The immunogen was derived by coupling the reactive acyl azide of 7-chloro-5(4-hydrazinocarbonylmethoxyphenyl)-2-methylamino-3H-1,4-benzodiazepine 4-oxide to BSA.

Spin labelling of benzodiazepinse for use in a Free Radical Assay Technique is disclosed by Goldstein et al. in U.S. Pat. No. 3,690,834. Specific benzodiazepines disclosed include chlordiazepoxide, diazepam and oxazepam.

Another paper, by Dixon et al., Pharm. 17, 251 (1975), describes a radioimmunoassay for clorazepam using an immunogen consisting of 3-hemisuccinoyloxyclorazepam covalently bound to BSA. The tracer employed for the assay was $^{3}H$-clorazepam. Sensitivity of the assay was 5 ng/ml using a 0.1 sample of plasma.

DESCRIPTION OF THE INVENTION

The present invention relates to an improved radioimmunoassay for clinically important benzodiazepine compounds such as; for example, diazepam, chlordiazepoxide, oxazepam, demoxepam and their metabolities. Unlike prior art radioimmunoassays for benzodiazepines, the present method employs $^{125}I$-labelled compounds as tracers. Such reagents are more convenient to prepare than the $^{14}C$ or $^{3}H$ labelled tracers of the prior art and allow the assayist to take advantage of the instrumentation and methodology advances which have taken place in clinical science in the area of $^{125}I$ radioimmunoassays particularly with respect to detection of drugs of abuse.

The radioiodinated compounds used as tracers in the present assay are conveniently prepared by iodinating in a manner known per se the corresponding 4'-hydroxy derivatives of the compounds to be assayed. A suitable iodinating procedure involves treatment of the 4'-hydroxy derivative with $^{125}I$ in the presence of Chloramine T (sodium p-toluene sulfonchloramide) preferably in the presence of sodium borate buffer pH 8.4. The radioiodinated product can be isolated using gel chromatography.

Antibodies useful in the present assay can be selected from those already known in the art. Thus, for example, antibodies directed specifically to diazepam and to both diazepam and its N-demethylated metabolite are described by Peskar and Spector cited above. Additionally, Dixon et al., cited above, disclose the preparation of an antibody specific to chlordiazepoxide.

Novel antibodies can also be employed in the practice of the present invention. Thus, for example, antibodies specific to oxazepam can be elicited in the usual manner by using an antigen obtained by covalently coupling the diazonium salt of the novel hapten 5-(4-aminophenyl)-7-chloro-1,3-dihydro-3-hydroxy-2H-1,4-benzodiazepin-2-one to a conventional immunogenic carrier material. As used herein the term "immunogenic carrier material" is meant to include those materials which have the property of independently eliciting an immunogenic response in a host animal and which can be covalently coupled via a diazo linkage to the aforesaid hapten. Suitable carrier materials include, for example, proteins, natural or synthetic polymeric compounds such as polypeptides, e.g., polylysine or copolymers of amino acids; polysaccharides; and the like. Particularly preferred carrier materials are proteins and polypeptides, especially proteins.

The identity of the protein material utilized in the preparation of an antigen of the instant invention is not critical. Examples of suitable proteins useful in the practice of this invention include mammalian serum protein such as, for example, human gamma globulin, human serum albumin, bovine serum albumin (BSA), methylated bovine serum albumin, rabbit serum albumin and bovine serum globulin. Bovine serum albumin is a preferred protein material. Other suitable protein materials will be suggested to one skilled in the art. It is generally preferred but not critically necessary that protein materials be utilized which are foreign to the animal hosts in which the resulting antigen will be employed.

The covalent coupling of the amino-benzodiazepine hapten to the carrier material can be carried out in a manner known per se. Thus the amino-benzodiazepine hapten can be diazotized by treatment with an alkali metal nitrite such as sodium nitrite in the presence of acid. Excess nitrite is destroyed such as by the addition of ammonium sulfamate solution. The resulting diazonium salt is coupled to the immunogenic carrier material by mixing the reactants at reduced temperature such as about 4° C. at a pH of about 8-9.

In a further aspect of the present invention novel antibodies specific to demoxepam can be elicited in a manner analogous to that described for oxazepam utilizing an antigen which is derived by diazotizing 5-(4-aminophenyl)-7-chloro-1,3-dihydro-2H-1,4-benzodiazepin -2-one4-oxide and coupling the hapten diazonium salt to a desired immunogenic carrier material as above.

The antigens hereinabove described may be utilized to induce formation of the desired specific antibodies in host animals by injecting the antigen in such a host animal, preferably using an adjuvant. Improved titers can be obtained by repeated injections over a period of time. Suitable host animals for this purpose include mammals such as rabbits, horses, goats, guinea pigs, rats, cows, sheep, etc. Rabbits are a preferred host animal. The resulting antisera will contain antibodies which will selectively complex with the target benzodiazepine. If desired, the antibodies can be purified and/or isolated from the antisera using procedures well known in the art. Such procedures include precipitation, column chromatography, gel chromatography electrophoresis and the like.

The antibodies described above are useful as reagents for the determination of select benzodiazepine compound concentrations in biological fluids, preferably serum. In one useful assay procedure, a known amount of labelled benzodiazepine is mixed with the above antibody and a sample containing an unknown concentration of the target benzodiazepine is added. The amount of the target benzodiazepine in the sample can be determined by measuring the inhibition of the binding to the specific antibody of the labelled benzodiazepine by the sample and comparing the value observed with a standard curve previously developed. The reagents may be added in any order. A suitable assay procedure for this purpose is described in greater detail in U.S. Pat. No. 3,709,868. Other assay procedures known in the art for carrying out radioimmunoassays can also be employed.

The present invention is further illustrated in the examples which follow.

EXAMPLE 1

Immunogen Preparation

Reagents
(1) Sodium borate buffer, 0.16 M, pH 9.0
(2) 0.1 N NaOH
(3) $NaHCO_3$, 0.05 M
(4) $NaNO_2$, 1 M
(5) $NH_4SO_3NH_2$(Ammonium sulfamate), 1.0 M
(6) 1 N HCl
(7) Bovine serum albumin (BSA)
(8) 5-(4-aminophenyl)-7-chloro-1,3-dihydro-2H-1,4-benzodiazepin-2-one-4-oxide
(9) Dimethyl formamide (DMF)

Procedure
(1) Diazotization

Dissolved 60.7 mg (about 200 μmol) of the 4'-amino derivative in 4.0 ml. DMF to addition of 0.8 ml of 1 N HCl. Cooled reaction mixture to about 4° C and added 0.2 ml of 1 M $NaNO_2$ with mixing. Continued mixing for 30 minutes at about 4° C. Added 50 μl of the ammonium sulfamate solution and mixed periodically for 5 minutes at the same temperature.

(2) Conjugation

Dissolved 701 mg (about 10 μmol) BSA in 20 ml of borate buffer (0.16 M, pH 9.0) and cooled to about 4° C prior to addition of the diazonium solution. The latter was added in portions with stirring, and the pH was maintained between 8-9 by addition of 0.1 N NaOH. Stirring was continued overnight at about 4° C.

Transferred the reaction mixture to a pre-washed dialysis bag and dialyzed against 0.5 M $NaHCO_3$ followed by $H_2O$. The dialyzed conjugate (color: red-brown) was freeze-dried and stored at about 4° C over desiccant. This material is useful in eliciting antibodies specific to demoxepam.

EXAMPLE 2

The procedure of Example 1 is followed with the exception that 5-(4-aminophenyl)-7-chloro-1,3-dihydro-3-hydroxy-2H-1,4-benzodiazepin-2-one is used as hapten. The resulting immunogen prepared by coupling the diazonium salt of the aforesaid hapten to BSA is useful in eliciting antibodies specific to oxazepam.

EXAMPLE 3

The procedure of Peskar and Spector, J. Pharmacol. Exp. Ther. 186, 167 (1973) was followed using 5-[3-(4-aminophenylazo)-4-hydroxyphenyl]-7-chloro-1,3-dihydro-1-methyl-2H-1,4-bezodiazepin-2-one as hapten. The resulting immunogen prepared by coupling the diazonium salt of the aforesaid hapten to BSA is useful in eliciting antibodies specific to diazepam.

EXAMPLE 4

The procedure of Dixon et al., J. Pharm. Sci. 64, 937 (1975) was followed using 7-chloro-5-(4-hydrazinocarbonylmethoxyphenyl)-2-methylamino-3H-1,4-benzodiazepine 4-oxide as hapten. The resulting immunogen prepared by coupling the active acyl azide of the aforesaid hapten to BSA is useful in eliciting antibodies specific to chlordiazepoxide.

EXAMPLE 5

Immunization Protocol for Production of Antibodies to Benzodiazepines

Animal species used: rabbit
Antigen:

Preparation I — 0.5 mg/ml suspension of immunogens of Examples 1, 2 and 3 while with the immunogen of Example 4, a 0.25 mg/ml suspension was used.

All conjugates except that of Example 4 were dissolved in 0.9% NaCl and emulsified in an equal volume of Freund's Complete Adjuvant. The Example 4 conjugate was dissolved in 0.45% NaCl prior to emulsification.

Preparation II — 0.1 mg/ml suspension of all immunogens.

All conjugates except that of Example 4 were dissolved in 0.9% NaCl and emulsified in an equal volume of Freund's Incomplete Adjuvant. The Example 4 conjugate was dissolved in 0.45% NaCl prior to emulsification.

Preparation III — 0.1 mg/ml solutions of all conjugates, except that of Example 4, were prepared in 0.9% NaCl. The Example 4 conjugate was dissolved in distilled water at the 0.1 mg/ml concentration.

Routes of administration:

Preparations I and II were given subcutaneously while Preparation III was administered intravenously.

Procedure:

Except for rabbits receiving the Example 4 immunogen, 0.25 ml of Preparation I, at a concentration of 0.5 mg of conjugate per milliliter, was injected at each of four sites above the subaxillary and inguinal lymph nodes. Preparation I of Example 4 was injected at a concentration of 0.25 mg/ml at eight sites. Injections were made weekly for 5-6 weeks, with frequent determination of antibody titers. All bleedings were taken by slitting the ear vein.

Preparation II was injected about six weeks after the initial injection and in the same manner as Preparation I. Two weeks after the injection of Preparation II, an injection of Preparation III into the ear vein was made. Fifty milliliters of blood were collected seven to ten days following this "booster" injection. Subsequent "booster" injections were made at monthly intervals followed, as above, by 50 ml bleedings.

EXAMPLE 6

Iodination of 4'-OH-1,4-benzodiazepine derivatives

Fifty microliters (about 0.17 μmol) of a 1 mg/ml solution of the 4'-OH derivative of chlorodiazepoxide, 7-chloro-5(4-hydroxyphenyl)-2-methylamino-3H-1,4-benzodiazepine 4-oxide in dimethylsulfoxide (DMSO), were added to a vial containing 5 mCi of carrierfree $^{125}$I. After mixing, 40 μl of Chloramine T (sodium p-toluene sulfonchloramide, 5 mg/ml in sodium borate buffer (0.05 M, pH 8.4) was added. The resulting reaction mixture was agitated for 1.5 min followed by the addition of 40 μl of sodium metabisulfite (10 mg/ml) in the sodium borate buffer. The mixture was then transferred to a 1.5 × 70 cm Bio-Gel P-2 polyacrylamide gel column which had been equilibrated with 0.1 Tris-HCl buffer, pH 7.4, containing 0.02% $NaN_3$ and 0.9% NaCl. This buffer was also used as eluent. Radioactive peaks eluted from the column were evaluated on the basis of percent radioactivity bound to antibody. Identical labelling procedures were employed in the iodination of 4' OH-diazepam (7-chloro-1,3-dihydro-5-(4-hydroxyphenyl)-1-methyl-2H-1,4-benzodiazepin-2-one), 4' OH-demoxepam (7-chloro-1,3-dihydro-5-(4-hydroxyphenyl)-2H-1,4-benzodiazepin-2-one-4-oxide) and 4' OH-oxazepam (7-chloro-1,3-dihydro-3-hydroxy-5-(4-hydroxyphenyl)-2H-1,4-benzodiazepin-2-one).

Although tubes containing labelled benzodiazepine were pooled on the basis of percent radioactivity bound to antibody, the entire peak was included in determining the indicated yields and specific activities:

| $^{125}$I Labelled Compound | Radioactivity in Peak % | Specific Activity μCi/μg |
|---|---|---|
| 4'-OH-chlordiazepoxide | 13.0 | 13 |
| 4'-OH-diazepam | 16.2 | 16 |
| 4'-OH-demoxepam | 53.6 | 54 |
| 4'-OH-oxazepam | 33.6 | 34 |

EXAMPLE 7

Radioimmunoassay (RIA)

Procedure for Chlordiazepoxide in Serum
Reagents:

| Item | Ingredients |
|---|---|
| 1 | Concentrated $^{125}$I-4'-hydroxy chlordiazepoxide |
| 2 | 0.1 M Tris-HCl buffer with 0.02% $NaN_3$, 0.9% NaCl pH = 7.3 |
| 3 | Normal rabbit serum |
| 4 | Rabbit antiserum |
| 5 | Stock chlordiazepoxide standard: 1000 ng/ml in normal human serum (Item 6) |
| 6 | Pooled normal human serum (chlordiazepoxide free) |
| 7 | Saturated ammonium sulfate solution |

Preparation:

1. Dilute the concentrated label (Item 1) 1:300 with 0.1 M Tris buffer (Item 2).
2. Prepare antiserum dilution as follows: 1:100 dilution - dilute 100 μl of rabbit antiserum (Item 4) to 10 ml with 9.9 ml of normal rabbit serum (Item 3).
3. Dilute stock chlordiazepoxide standard (Item 5) as follows in order to make chlordiazepoxide standards:

| Chlordiazepoxide Concentration (ng/ml) | μl of Stock Standard Solution(Item 5) | μl Normal Human Serum(Item 6) |
|---|---|---|
| 0 | — | 4000 |
| 50 | 200 | 3800 |
| 100 | 400 | 3600 |
| 200 | 800 | 3200 |

4. Place 800 g. of ammonium sulfate $(NH_4)_2SO_4$ in a 1 liter graduated Erlenmeyer flask. Bring to volume with distilled water. Keep in boiling water bath for 1 hr. while stirring. Cool overnight at 4° C before use.

Assay Procedure:

All assays are preformed in duplicate employing 12 × 75 mm borosilicate glass test tubes.
The assay requires the following groups of tubes:
group T: for determination of total activity
group NSB: for determination of non-specific binding
group STD: for the four points on the standard curve
group U: for unknown samples Step (1)

Distribute the reagents according to the following schedule:

| Group | 1:100 antiserum μl | Normal rabbit serum μl | 0.1 M Tris buffer μl | Chlordiazepoxide standards μl | Normal human serum μl | Unknown sample μl | $^{125}$I- 4'-hydroxy chlordiazepoxide μl |
|---|---|---|---|---|---|---|---|
| T | — | — | 800 | — | — | — | 200 |
| NSB | — | 200 | — | — | 100 | — | 200 |
| STD | 200 | — | — | 100 | — | — | 200 |
| U | 200 | — | — | — | ' | 100 | 200 |

Step (2)

Mix the contents of each tube on a Vortex mixer and incubate at room temperature for 30 minutes.

Step (3)

Add 0.5 ml of saturated ammonium sulfate (Item 7) to all tubes except those of group T.

Step (4)

Vortex each tube immediately after $(NH_4)_2SO_4$ addition and incubate 10-20 minutes at ambient temperature.

Step (5)

Centrifuge all tubes at 3000 RPM for 10 minutes to pack precipitates.

Step (6)

Count 0.5 ml of the clear supernatant from each tube in a gamma scintillation counter for 1 minute.

Step (7)

Step up standard curve as follows: Plot cpm on the Y (vertical) axis versus ng chlordiazepoxide on the X (horizontal) axis.

Step (8)

Determine average cpm for each unknown sample tested. Interpolate from ordinate to standard curve in order to determine ng of chlordiazepoxide in 100 μl of tested serum.

Step (9)

Sample calculation:
Interpolated ng/100 μl × 10 = ng chlordiazepoxide/ml

The aforesaid procedure can also be employed for assaying for oxazepam, demoxepam and diazepam by substituting the appropriate antisera, standard and $^{125}$I-labelled-4'-hydroxy derivative compound into the subject procedure.

EXAMPLE 8

2-Amino-5-chloro-4'-hydroxybenzophenone

To a solution of 83.7 g (0.34 mole) of 5-chloro-3-(4-hydroxyphenyl)-2,1-benzisoxazole in 1500 ml of glacial acetic acid was added 45 g of iron filings. The mixture was stirred and heated on the steam bath for 20 min. Every 30 min. an additional 20 g of iron filings and 100 ml of water was added for 2.5 hr. After 30 min. more, the reaction mixture was filtered while hot. The collected precipitate was heated with acetic acid and filtered. The combined filtrates were diluted with ice water to precipitate 39.8 g (47%) of product, mp 170°–175°. Recrystallization from methanol-water gave yellow rods, mp 173°–178°.

EXAMPLE 9

2-Bromo-4'-chloro-2'-(4-hydroxybenzoyl)acetanilide

A solution of 41 g (0.165 mole) 2-amino-5-chloro-4'-hydroxybenzophenone in 800 ml of ether and 200 ml of water was cooled to 5°. The mixture was stirred while 20 ml (0.277 mole) of bromoacetyl bromide and a 20% solution of sodium carbonate were added alternately keeping the solution slightly basic. After 20 min. the reaction mixture was filtered to collect 60 g (about 100%) of product mp 201°–202°. Recrystallization from ethanol gave colorless prisms, mp 201°–203°.

Anal.-Calc. for $C_{15}H_{11}BrClNO_3$: C, 48.87; H, 3.01; Tot. hal., 31.30. Found: C, 49.17; H, 3.34; Tot. hal., 30.84.

EXAMPLE 10

7-Chloro-1,3-dihydro-5-(4-hyroxyphenyl)-2H-1,4-benzodiazepin-2-one

To 350 ml of liquid ammonia was added 60 g (0.163 mole) of 2-bromo-4'-chloro-2'-(4-hydroxybenzoyl)acetanilide. After refluxing for 3 hr, the ammonia was allowed to evaporate. The residue was heated to reflux in 400 ml of ethanol for 3 hr. Ethanol was evaproated, and 800 ml of acetone was added. This suspension was heated and filtered to remove inorganic salts. Concentration of acetone filtrate gave 31.5 g (67%) of product, mp 271°–272°.

Anal. Calc. for $C_{15}H_{11}ClN_2O_2$: C, 62.84; H, 3.87; N,9.77 Found: C, 62.52; H, 4.13; N, 9.92.

EXAMPLE 11

7-Chloro-1,3-dihydro-5-(4-hydroxyphenyl)-1-methyl-2H-1,4-benzodiazepin-2-one To a solution of 6.5 g (0.022 mole) of 7-chloro-1,3-dihyro-5-(4-hydroxyphenyl)-2H-1,4-benzodiazepin-2-one in 40 ml of dimethylformamide was added 11.6 ml (0.055 mole) of 4.74 M sodium methoxide in methanol. After 90 min, the mixture was cooled in an ice bath and 9.4 g (0.066 mole) of methyl iodide was added dropwise with stirring. After 18 hr at room temperature the reaction mixture was acidified with acetic acid, and partitioned between 100 ml of dichloromethane and 100 ml of water. The water layer was extracted once more with dichloromethane. The combined dichloromethane extracts were evaporated to dryness. The residual product mixture was separated on a column of Florisil. The column was eluted with dichloromethane, ether and then ethyl acetate. The ethyl acetate fraction was evaporated and crystallized from methanol to give 0.40 g (6%) of product as colorless prisms, mp 225°–259°.

Anal. Calc. for $C_{16}H_{13}ClN_2O_2$: C, 63.90; H, 4.35; N, 9.31. Found: C, 63.89; H, 4.29; N, 9.46.

EXAMPLE 12

6-Chloro-2-chloromethyl-4-(4-hydroxyphenyl)quinazoline 3-oxide

A solution of 40.5 g (0.12 mole) 2,4'-dichloro-2'-(4-hydroxybenzoyl)-acetanilide oxime and 40.5 mg (0.329 mole) of boron trifluoride etherate was heated to reflux. After 5 hr, it was cooled and 200 ml of water was added. The dioxane was removed by distillation and the reaction mixture was made basic with a 5% sodium bicarbonate solution. The solid was collected, heated in methanol at reflux for a few minutes, cooled and collected to give, in two crops, 21.3 g (56%) of product. An analytical sample which was recrystallized from methanol melted at 226°–227° dec.

Anal. Calc. for $C_{15}H_{10}Cl_2N_2O_2$: C, 56.10; H, 3.14; N, 8.72. Found: C, 56.26; H, 2.81; N, 9.01.

EXAMPLE 13

7-Chloro-5-(4-hydroxyphenyl)-2-methylamino-3H-1,4-benzodiazepine 4-oxide

To a saturated solution of methylamine in 600 ml of methanol in an ice bath was added 19.2 g (0.60 mole) of 6-chloro-2-chloromethyl-4-(4-hydroxyphenyl) quinazoline 3-oxide. The solution was stirred for 7 hr in an ice bath, and 10 hr at room temperature and then evaporated under reduced pressure. The residue was acidified with dilute acetic acid, stirred with ether and filtered to give 19 g of product. Recrystallization for analysis from ethyl acetate gave colorless plates, mp 278°–279° dec.

Anal. Calc. for $C_{16}H_{14}ClN_3O_2$: C, 60.86; H, 4.47; N, 13.30. Found: C, 61.23; H, 4.74; N, 13.14.

EXAMPLE 14

3-(4-Aminophenyl)-5-chloroanthranil

To a mixture of 100 g (0.662 mole) of o-nitrobenzaldehyde and 160 g (1.05 mole) of phosphorus oxychloride was added dropwise with stirring 100 g (1.08 mole) of aniline, keeping the temperature below 30°. After 3 hr. at room temperature it was heated to 75° for 18 hr. and at 90° for 3 hr. (The reaction becomes exothermic when heated). The mixture was cooled, 200ml of ethanol and 200 ml of concentrated hydrochloric acid were added, then heated to reflux for 3 hr. with stirring. On cooling, the precipitate formed was collected and washed with acetone, then resuspended in dilute ammonium hydroxide for 1 hr. and collected again. After crystallization from ethanol, 70 g (86%) of product was obtained. Recrystallization from ethanol gave orange rods, mp 208°–211°.

EXAMPLE 15

4′-(5-chloro-3-anthranilyl)-2,2,2-trifluoroacetanilide

A mixture of 70 g (0.286 mole) of 3-(4-aminophenyl)-5-chloroanthranil, 75 g (0.357 mole) trifluoroacetic anhydride and 1 l. of tetrahydrofuran was heated to reflux for 30 min. After concentrating to a small volume, ether (300 ml) was added. The solution was filtered to give 60 g of product, and then concentrated to give an additional 5 g. The filtrate was evaporated and the residue was stirred with cold aqueous potassium carbonate solution and filtered. The solid thus collected was dissolved in tetrahydrofuran, treated with charcoal, and after filtering and concentrating to a small volume, ether was added. A precipitate of 10 g of product was collected to give a total yield of 75 g (77%). A sample recrystallized from a mixture of tetrahydrofuran and hexane gave pale yellow rods, mp 251°–254°, ir (KBr) 3310 (NH) 1705 cm$^{-1}$ (C=O).

Anal. Calc. for $C_{15}H_8ClF_3N_2O_2$: C, 52.88; H, 2.37; N, 8.22. Found C, 52.85; H, 2.32; N, 8.27.

EXAMPLE 16

2-Amino-5-chloro-4′-(2,2,2-trifluoroacetamido)-benzophenone

To a solution of 75 g (0.220 mole) of 4′-(5-chloro-3-anthranilyl-2,2,2-trifluoroacetanilide in 1300 ml of glacial acetic acid was added 100 g of iron filings. The reaction was heated with stirring for 20 min on the steam bath, and then another 50 g of iron filings was added. After 30 min an additional 50 g of iron filings was added and after 30 min. the reaction was filtered while hot. Ice water was added to the filtrate precipitating 66 g (88%) of product. A sample was recrystallized from methanol to give yellow needles of product which crystallized as a methanolate, mp 65°–75°, reset 148°–149°; ir (CHCl$_3$) 3500, 3420 (NH$_2$) 1740, 1634 cm$^{-1}$ (2 C=O).

Anal. Calc. for $C_{15}H_{10}ClF_3N_2O_2 CH_3OH$: C, 51.28; H, 3.77; N, 7.48. Found: C, 51.19; H, 3.71; N, 7.35.

EXAMPLE 17

2-(Bromoacetamido)-5-chloro-4′-(2,2,2-trifluoroacetamido)-benzophenone

To a stirred mixture of 56 g (0.163 mole) of 2-amino-5-chloro-4′-(2,2,2-trifluoroacetamido)-benzophenone in 900 ml of ether was added 43 g (0.213 mole) of bromoacetyl bromide and a saturated aqueous solution of sodium bicarbonate in portions, keeping the solution slightly basis during the addition. The reaction was stirred for 90 min and filtered to give 66 g of product. The ether layer was dried and evaporated and the residual oil was crystallized from methanol to give an additional 10 g of the product for a total yield of 76 g (96%). Recrystallization from a mixture of dichloromethane, methanol and petroleum ether gave an analytical sample of off white rods, mp 198°–201° ir (KBr) 1750, 1663, 1640 cm$^{-1}$ (3C=O).

Anal. Calc. for $C_{17}H_{11}BrClF_3N_2O_3$: C, 44.03; H, 2.39; N, 6.04. Found: C, 44.22; H, 2.56; N, 6.03.

EXAMPLE 18

7-Chloro-1,3-dihydro-5-[4-(2,2,2-trifluoroacetamidophenyl)]-2H-1,4-benzodiazepin-2-one A solution of 90 g (0.194 mole) of 2-(bromoacetamido)-5-chloro-4′-(2,2,2-trifluoroacetamido)-benzophenone in a mixture of 900 ml of tetrahydrofuran and 900 ml of ethyl acetate, was stirred in an ice bath, and saturated with a stream of ammonia gas over the period of 1 hr. The mixture was allowed to stand overnight at room temperature and then filtered. The filtrate was evaporated and the residue was partitioned between dichloromethane and water. The mixture obtained from evaporation of the dichloromethane layer was heated to reflux in 400 ml of ethanol for 3 hr. The solution was concentrated, cooled and filtered to give 32 g (43%) of product. A sample was recrystallized from dichloromethane-ether to give colorless prisms, which reset on heating to from needles, mp 273°–276°; ir (KBr) 1730, 1678 cm$^{-1}$ (2 C=O).

Anal. Calc. for $C_{17}H_{11}ClF_3N_3O_2$: C, 53.49; H, 2.90; N, 11.00. Found: C, 53.63; H, 2.92; N, 10.85.

EXAMPLE 19

7-Chloro-1,3-dihydro-5-[4-(2,2,2-trifluoroacetamido)-phenyl]-2H-1,4-benzodiazepin-2-one 4-oxide To a mixture of 31.5 g (0.0825 mole) of 7-chloro-1,3-dihydro-5-[4-(2,2,2-trifluoroacetamidophenyl]-2H-1,4-benzodiazepin-2-one in 1.8 l. of dichloromethane was added with stirring 30 g (0.147 mole) of 85% m-chloroperbenzoic acid. After 18 hr, 500 ml of cold water was added and the solution was made basic with ammonium hydroxide. The crystalline product was collected on a filter. The dichloromethane was concentrated for a second crop, giving a total yield of 21.5 g (66%). Recrystallization from dichloromethane-methanol gave off-white rods, mp 295°–297° dec; ir (KBr) 1698 (broad 2 C=O).

Anal. Calc. for $C_{17}H_{11}ClF_3N_3O_3$: C, 51.33; H, 2.79; N, 10.57. Found: C, 51.32; H, 2.57; N, 10.44.

EXAMPLE 20

5-(4-Aminophenyl)-7-chloro-1,3-dihydro-2H-1,4-benzodiazepin-2-one 4-oxide

To a solution of 1.0 g (2.51 mmole) of 7-chloro-1,3-dihydro-5-[4-(2,2,2-trifluoroacetamido) phenyl]-2H-1,4-benzodiazepin 2-one 4-oxide in 25 ml of methanol was added 20 ml (20 mmole) of 1 N sodium hydroxide. After 15 min, 20 ml of water was added. The reaction mixture was allowed to stand for 3 hr, acidified with acetic acid and the methanol was removed in vacuo. The mixture was made basic with ammonium hydroxide and filtered. Recrystallization from tetrahydrofuran-methanol gave 0.30 g (39%) of pale yellow rods, mp 256°–258°; ir (KBr) 3415, 3350, 3245 (NH$_2$, NH), 1700 cm$^{-1}$ (C=O); mass spectrum m/e 301 (M+).

Anal. Calc. for $C_{15}H_{12}ClN_3O_2$: C, 59.71; H, 4.10; N, 13.93. Found: C, 59.52; H, 4.02; N, 13.73.

EXAMPLE 21

3-Acetoxy-7-chloro-1,3-dihydro-5-[4-(2,2,2-trifluoroacetamido) phenyl]-2H-1,4-benzodiazepin-2-one A mixture of 14 g (0.0352 mole) of 7-chloro--1,3-dihydro- 5-[4-(2,2,2-trifluoroacetamido) phenyl]-

2H1,4-benzodiazepin-2-one 4-oxide in 200 ml of tetrahydrofuran and 400 ml of acetic anhydride was heated on the steam bath of 2 hr. The mixture was evaporated under reduced pressure. Crystallization of the residue from methanol afforded 8.3 g of product. A second crop of 5.3 g was obtained from ether-hexane thus giving a total yield of 13.5 g (87.7%). Recrystallization from a mixture of tetrahydrofuran, dichloromethane, and hexane gave white prisms, mp 257°–262°; ir (KBr) 1740, 1720, 1688 cm$^{-1}$ (3 C=O); mass spectrum m/e 439 (M$^{30}$).

Anal. Calc. for $C_{19}H_{13}ClF_3N_3O_4$: C, 51.89; H, 2.98; N, 9.56. Found: C, 51.36; H, 2.99; N, 9.23.

EXAMPLE 22

5-(4-Aminophenyl)-7-chloro-1,3-dihydro-3-hydroxy-2H-1,4-benzodiazepin-2-one

To a solution of 0.60 g (1.3 mmole) of 3-acetoxy-7-chloro-1,3-dihydro-5-[4-(2,2,2-trifluoroacetamido) phenyl]-2H-1,4-benzodiazepin-2-one in 25 ml of methanol was added 20 ml of 1N sodium hydroxide, followed by the addition of 20 ml of water after 1 hr. The reaction mixture was filtered after 3 hr. The filtrate was acidified with acetic acid and then made slightly basic with ammonium hydroxide. It was extracted with dichloromethane (2 × 100 ml), which was dried and concentrated to a small volume. Product that crystallized was collected. Recrystallization from tetrahydrofruanmethanol afforded 0.20 g (50%) of yellow prisms, mp above 350° ir (KBr) 3455, 3375 (NH$_2$NH), 3225, 3160 (OH), 1713, 1698 cm$^{311}$ (split C=O); NMR (Me$_2$SO-d$_6$) δ 10.60 (1H, s, NH), 6.02 (1H,d,OH), 5.58 (2H,s,NH$_2$), 4.64 (1H,d,CH); mass spectrum m/e 301 (M$^+$).

Anal. Calc. for $C_{15}H_{12}ClN_3O_2$: C, 59.71; H, 4.00; N, 13.93. Found: C, 59.33; H, 4.46; N, 14.03.

We claim:

1. In a method for the radioimmunoassy for a 1,4-benzodiazepine compound or metabolites thereof in a sample, which method comprises mixing said sample with a known amount of a labelled 1,4-benzodiazepine compound and an antibody which will selectively bind said 1,4-benzodiazepine compound and said labelled 1,4-benzodiazepine compound, measuring the degree of binding of the said labelled 1,4-benzodiazepine compound to said antibody, and determining the amount of said 1,4-benzodiazepine compound in said sample by comparing said degree of binding to a standard curve; the improvement which comprises utilizing a $^{125}$I-4'-hydroxy-1,4-benzodiazepine as said labelled compound.

2. The method of claim 1 wherein said 1,4-benzodiazepine compound is chloridazepoxide and said labelled compound is $^{125}$I-4'-hydroxy-chlordiazepoxide.

3. The method of claim 1 wherein said 1,4-benzodiazepine compound is diazepam and said labelled compound is $^{125}$I-4'-hydroxy-diazepam.

4. The method of claim 1 wherein said 1,4-benzodiazepine compound is oxazepam and said labelled compound is $^{125}$I-4'-hydroxy-oxazepam.

5. The method of claim 1 wherein said 1,4-benzodiazepine compound is demoxepan and said labelled compound is $^{125}$I-4'-hydroxy-demoxepam.

6. $^{125}$I-4'-hydroxy-chlordiazepoxide.

7. $^{125}$I-4'-hydroxy-diazepam.

8. $^{125}$I-4'-hydroxy-oxazepam.

9. $^{125}$I-4'-hydroxy-demoxepam.

10. A composition consisting essentially of the reaction product of the diazonium salt of 5-(4-aminophenyl)-7-chloro-1,3-dihydro-2H-1,4-benzodiazepin-2-one 4-oxide and an immunogenic carrier material.

11. The composition of claim 10 wherein said immunogenic carrier material is bovine serum albumin.

12. A composition consisting essentially of the reaction product of the diazonium salt of 5-(4-aminophenyl)-7-chloro-1,3-dihydro-3-hydroxy-2H-1,4-benzodiazepin-2-one and an immunogenic carrier material.

13. The composition of claim 12 wherein said immunogenic carrier material is bovine serum albumin.

14. An antibody specific to demoxepam said antibody being prepared by innoculating a host animal with an immunogen comprising the reaction product of the diazonium salt of 5-(4-aminophenyl)-7-chloro-1,3-dihydro-2H-1,4-benzodiazepin-2-one 4-oxide and an immunogenic carrier material to elicit said antibody in the serum of said host animal and collecting serum from said host animal.

15. An antibody specific to oxazepam said antibody being prepared by innoculating a host animal with an immunogen comprising the reaction product of the diazonium salt of 5-(4-aminophenyl)-7-chloro-1,3-dihydro-3-hdyroxy-2H-1,4-benzodiazepin-2-one and an immunogenic carrier material to elicit said antibody in the serum of said host animal and collecting serum from said host animal.

* * * * *